(12) United States Patent
Chatterjee et al.

(10) Patent No.: US 8,585,880 B2
(45) Date of Patent: Nov. 19, 2013

(54) METHOD AND APPARATUS FOR SIMULTANEOUS SPECTROELECTROCHEMICAL ANALYSIS

(75) Inventors: Sayandev Chatterjee, Richland, WA (US); Samuel A. Bryan, Richland, WA (US); Cynthia A. Schroll, Kettering, OH (US); William R. Heineman, Cincinnati, OH (US)

(73) Assignee: Battelle Memorial Institute, Richland, WA (US)

( * ) Notice: Subject to any disclaimer, the term of this patent is extended or adjusted under 35 U.S.C. 154(b) by 240 days.

(21) Appl. No.: 13/246,090

(22) Filed: Sep. 27, 2011

(65) Prior Publication Data
US 2013/0075275 A1 Mar. 28, 2013

(51) Int. Cl.
*G01N 21/75* (2006.01)
(52) U.S. Cl.
USPC ............................................ 204/412; 356/72
(58) Field of Classification Search
USPC ............. 204/400, 407, 412; 356/72, 319–322
See application file for complete search history.

(56) References Cited

U.S. PATENT DOCUMENTS 3,947,124 A * 3/1976 West .............................. 356/300
6,015,479 A * 1/2000 Boss et al. .................... 204/412

OTHER PUBLICATIONS

Anderson, C.W., et al. "A small-volume thin-layer spectroelectrochemial cell for the study of biological components" Analytical Biochemistry, vol. 93, 1979, p. 366-372.*
Comtat, Maurice, et al., "Some Examples of the Use of Thin Layer Spectroelectrochemistry n the Study of Electron Transfer Between Metals and Enzymes, Biosensors & Bioelectronics," 1994, vol. 9, pp. 663-668.
Krenitsky, Thomas A., et al., "A Comparison of the Specificities of Xanthinke Oxidase and Aldehyde Oxidase," 1972, Archives of Biochemistry and Biophysics, vol. 160, pp. 585-599.
Wijayawardhana, C. Ajith, et al., "Micro Volume Rotating Disk Electrode (RDE) Amperometric Decection for a Bead-Based Immunoassay," 1999, Analytica Chimica Acta, vol. 399, pp. 3-11.
Porter, Marc D., et al., "Spectroelectrochemical Cell with Adjustable Solution Layer Thickness," 1984, Anal. Chem., vol. 56, pp. 2263-2265.
Winograd, Nicholas, et al., "High Sensitivity Internal Reflection Spectroelectrochemistry for Direct Monitoring of Diffusins Species Using Signal Averaging," 1971, Analytical Chemistry, vol. 43, No. 2, p. 252.

(Continued)

*Primary Examiner* — J. Christopher Ball
(74) *Attorney, Agent, or Firm* — A. J. Gokcek (57) ABSTRACT

An apparatus and method of simultaneous spectroelectrochemical analysis is disclosed. A transparent surface is provided. An analyte solution on the transparent surface is contacted with a working electrode and at least one other electrode. Light from a light source is focused on either a surface of the working electrode or the analyte solution. The light reflected from either the surface of the working electrode or the analyte solution is detected. The potential of the working electrode is adjusted, and spectroscopic changes of the analyte solution that occur with changes in thermodynamic potentials are monitored.

30 Claims, 9 Drawing Sheets

(56) References Cited

OTHER PUBLICATIONS

Heineman, William R., et al., "Spectroelectrochemical Studies of Metal Deposition and Stripping of Specific Adsorption on Mercury-Platinum Optically Transparent Electrodes," 1972, Analytical Chemistry, vol. 44, No. 12, pp. 1972-1978.

Heineman, William R., "Measurement of Enzyme $E^{0'}$ Values by Optically Transparent Thin Layer Electrichemical Cells," 1975, Analytical Chemistry, vol. 47, No. 1, pp. 79-84.

Heineman, William R., "Spectroelectrochemistry Combination of Optical and Electrochemical Techniques for Studies of Redox Chemistry," 1978, Analytical Chemistry, vol. 50, No. 3, pp. 390A-402A.

Wijayawardhana, C. Ajith, et al., "Micro Volume Rotating Disk Electrode (RDE) Amperometric Detection for a Bead-Based Immunoassay," 1999, Analytica Chimica Acta, vol. 399, pp. 3-11.

\* cited by examiner

METHOD AND APPARATUS FOR SIMULTANEOUS SPECTROELECTROCHEMICAL ANALYSIS

STATEMENT REGARDING FEDERALLY SPONSORED RESEARCH OR DEVELOPMENT

The invention was made with Government support under Contract DE-AC05-76RL01830, awarded by the U.S. Department of Energy. The Government has certain rights in the invention.

TECHNICAL FIELD

This invention relates to spectroelectrochemistry. More specifically, this invention relates to simultaneous spectroelectrochemical analysis by correlating spectroicopic properties with thermodynamic potentials on a small scale.

BACKGROUND OF THE INVENTION

Over the last several decades spectroelectrochemistry has gained considerable importance as an analytical technique for measuring, simultaneously the redox and spectral properties of inorganic, organic, and biological species. Spectroelectrochemistry can be implemented in cells that are characterized by either semi-infinite linear diffusion (SILD) in a bulk solution or by thin layer (TL) cells in which complete electrolysis is rapidly achieved in a thin layer of solution. The spectroscopic methods that have been used rely on light propagation through the sample based on transmission, specular reflection or internal reflection. In transmission spectroscopy, a light beam is passed through an optically transparent electrode and the sample. In specular reflection spectroscopy the light is passed through the sample, reflected off the electrode surface and then back through the sample. In internal reflection spectroscopy the light is directed into a wave guide at an angle less than the critical angle so that it is internally reflected. At each reflection point an evanescent electromagnetic wave interacts with the sample and changes in the spectra can be measured.

Spectroelectrochemistry has been used for a wide range of applications. In spite of the broad scope of both SILD and TL spectroelectrochemistry, wide applicability of the technique is limited by cell designs that are complicated to construct and use and that require relatively large sample sizes—on the order of milliliters.

What is needed is an electrochemical technique keeping the total sample volume as small as possible to obtain electrochemical information as half-wave potentials and diffusion coefficients. What is also needed is a technique of electrochemical detection with simultaneous spectroscopic detection in order to acquire spectroelectrochemical data in an easy and rapid way. What is further needed is a method and apparatus for lowering the distance between the working electrode and the transparent surface that contains the analyte solution so as to create a thin-layer spectroelectrochemistry environment. This technique and environment will allow for acquisition of spectroelectrochemical data in an easy, rapid and economic way and determine redox potentials.

SUMMARY OF THE INVENTION

The present invention is directed to an apparatus and method of simultaneous spectroelectrochemical analysis. In one embodiment of the present invention, an apparatus is disclosed. The apparatus comprises a transparent surface. The apparatus further comprises a working electrode, a reference electrode, and an auxiliary electrode, wherein the electrodes are in working contact with an analyte solution on the transparent surface. The apparatus also comprises a light source for focusing light on a surface of the working electrode; and a detector for receiving the light reflected from the surface of the working electrode.

In one embodiment, the apparatus further comprises a cusp of customized volume to contain the analyte solution on the transparent surface. The light is, but not limited to, visible light, ultraviolet (UV) light, near infrared (NIR) or combinations thereof. The light can be transmitted via a fiber optic cable. In one embodiment, the transparent surface is a transparent slide, made of glass or quartz.

In one embodiment, the apparatus further comprises a first channel for placement of the reference electrode and a second channel for placement of the auxiliary electrode. The apparatus can also comprise a fastener for fixing in place the working electrode perpendicular to the transparent surface, and a fastener for securing and providing electrical contact to the reference and auxiliary electrodes. In one embodiment, the reference and auxiliary electrodes are spaced from approximately 0.1 mm to approximately 3.0 millimeters apart from one another. In one embodiment, the working electrode is positioned within approximately 1 millimeter from the transparent surface.

In another embodiment of the present invention, a method of simultaneous spectroelectrochemical analysis is disclosed. The method comprises providing a transparent surface and contacting an analyte solution on the transparent surface with a working electrode, a reference electrode, and an auxiliary electrode. The method further comprises focusing light from a light source on a surface of the working electrode. The method also comprises detecting the light reflected from the surface of the working electrode. In one embodiment, the method includes adjusting a potential of the working electrode and monitoring spectroscopic changes of the analyte solution that occur with changes in thermodynamic potentials.

In another embodiment of the present invention, a method of simultaneous spectroelectrochemical analysis is disclosed. The method comprises providing a transparent surface and contacting an analyte solution on the transparent surface with a first electrode and a second electrode. The method also comprises focusing light from a light source on either a surface of the first electrode or the analyte solution. The method further comprises detecting the light reflected from either the surface of the first electrode or the analyte solution.

In another embodiment of the present invention, an apparatus for simultaneous spectroelectrochemical analysis is disclosed. The apparatus comprises a transparent surface and a first electrode and a second electrode, wherein the electrodes are in contact with an analyte solution on the transparent surface. The apparatus further comprises a light source for focusing light on either a surface of the first electrode or the analyte solution. The apparatus also comprises a detector for receiving the light reflected from either the surface of the first electrode or the analyte solution.

DETAILED DESCRIPTION OF THE PREFERRED EMBODIMENTS

Figure 1:
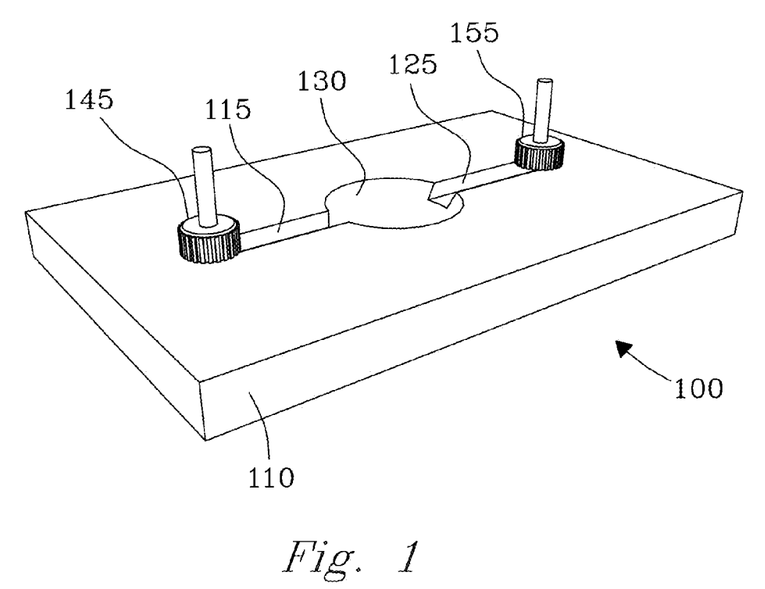
FIG. 1 is an illustration of an apparatus for simultaneous spectroelectrochemical analysis, in accordance with one embodiment of the present invention.

FIG. 1 is an illustration of an apparatus 100 for simultaneous spectroelectrochemical analysis, in accordance with one embodiment of the present invention. The apparatus 100 comprises a transparent surface 110, a first channel 115 for placement of a first electrode (not shown), a second channel 125 for placement of a second electrode (not shown), and a cusp 130 for containment of an analyte solution. The apparatus 100 also includes a first fastener 145 for securing and providing electrical contact to the first electrode, and a second fastener 155 for securing and providing electrical contact to the second electrode. In one embodiment, the first and second fasteners 145 and 155 are thumb-screws. The apparatus further includes a working electrode (not shown), a light source (not shown), and a detector (not shown).

In one embodiment, the transparent surface 110 is a transparent slide. The transparent slide can be made of, but not limited to, glass or quartz. The cusp 130, which is made of a customized volume to contain the analyte solution on the transparent surface 110, and can be any shape or size.

In one embodiment, the first electrode is a reference electrode and the second electrode is an auxiliary (or counter) electrode. The terms auxiliary electrode and counter electrode may be used interchangeably. In some embodiments, the first and second electrodes can be replaced by a reference/auxiliary electrode combination. The working electrode, the reference electrode, and the auxiliary electrode or the working electrode and the reference/auxiliary electrode combination are in contact with the analyte solution on the transparent surface 110. The apparatus 100 can also include a fastener (not shown) for fixing in place the working electrode perpendicular to the transparent surface 110. In one embodiment, the reference and auxiliary electrodes are spaced from approximately 0.1 mm to approximately 3.0 millimeters apart from one another. In one embodiment, the working electrode is positioned within approximately 1 millimeter from the transparent surface 110.

The light source focuses light on either a surface of the working electrode or the analyte solution. The light can be, but is not limited to, visible light, ultraviolet (UV) light, near infrared (NIR) or combinations thereof. In one embodiment, the light is transmitted via a fiber optic cable. The detector receives light reflected from either the surface of the working electrode or the analyte solution.

Once the solution is placed in the slide, the reference and auxiliary electrodes placed in the channels 115 and 125 and secured with the fasteners 145 and 155, the working electrode fixed to a clamp or other fastener, and the light source and detector hooked up to the apparatus 100, a spectrum is recorded. The spectrum—either absorbance or emission—is recorded at zero potential. The electrodes, which are connected to an electrical connection, are set to a particular potential and changes in spectroscopy are observed. The potentials are adjusted up or down until changes in the spectrum are recorded. The potential of the working electrode is adjusted and spectroscopic properties of the solution are correlated with thermodynamic potentials. Thus, the initial spectroscopy, final spectroscopy and electrochemistry are detected and recorded continuously while the potentials are adjusted and the light is transmitted through and reflected off the sample to the detector.

Figure 2A:
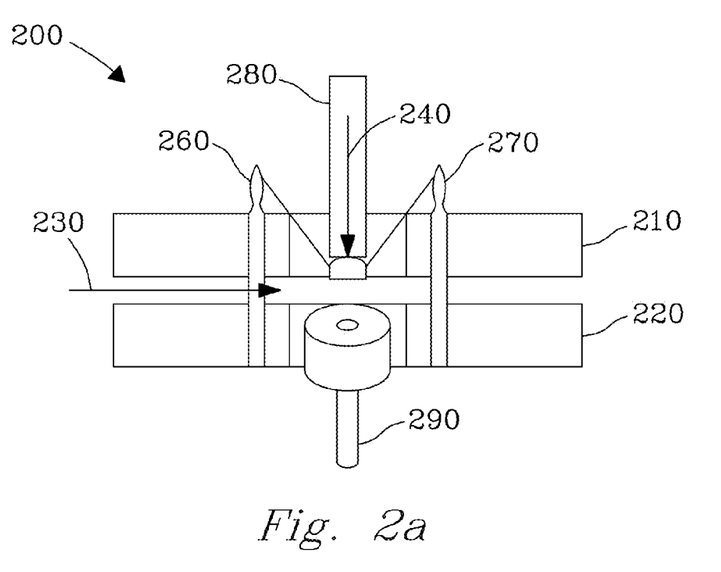
FIG. 2a is an illustration of an apparatus for simultaneous spectroelectrochemical analysis, in accordance with an alternative embodiment of the present invention.

FIG. 2A is an illustration of an apparatus 200 for simultaneous spectroelectrochemical analysis, in accordance with an alternative embodiment of the present invention. The apparatus 200 comprises a top plate 210 and a bottom plate 220 separated by a spacer (not shown) to allow an optically transparent surface, such as a quartz plate or glass microscope slide 230, to slide in between the plates 210 and 220. A hole is drilled at the center of the plates 210 and 220 to permit passage of an optical beam from a light source 290. The apparatus 200 also comprises a reference electrode 260, an auxiliary electrode 270 and a working electrode 280. The top plate 210 is held in place with a fastener, such as a thumb screw, that also provides conducting surfaces to attach the reference electrode 260 and the auxiliary electrode 270. The auxiliary electrode 270 and the reference electrode 260 are spaced approximately 0.1 to approximately 3.0 millimeters apart from one another. The working electrode 280 is lowered to within approximately 1 mm to 2 mm from the optically transparent surface, and an analyte solution 240 is placed in between. In one embodiment, the analyte solution 240 is a drop of solution, ranging from 1 µL to 100 µL. The drop is positioned to cover the reference electrode 260 and the auxiliary electrode 270, while surface tension ensures it contact with the working electrode from above. In one embodiment, the light source 290, such as a visible, UV or NIR probe with a bundle of fiber-optic cables, is fixed to a clamp below the optically transparent surface for spectral measurement and focused directly on the surface of the working electrode 280 or the drop of solution 240. In one embodiment, the reflectance probe configuration included fiber optic cables for excitation coming from the light source, with one concentrically located cable for collection of the light transmitted after reflection from the surface of the working electrode 280 or the solution 240, proceeding to a detector (not shown).

Figure 2B:
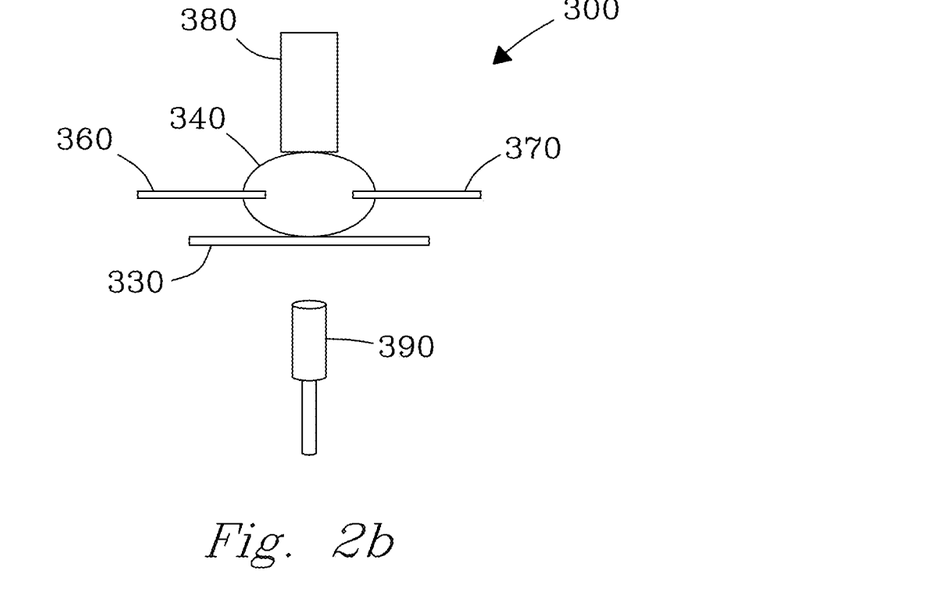
FIG. 2b is an illustration of an apparatus for simultaneous spectroelectrochemical analysis for semi-infinite diffusion set-up to measure diffusion coefficients, in accordance with an alternative embodiment of the present invention.

FIG. 2B is an illustration of an apparatus 300 for simultaneous spectroelectrochemical analysis for semi-infinite diffusion set-up to measure diffusion coefficients, in accordance with an alternative embodiment of the present invention. The apparatus 300 comprises a working electrode 380, a reference electrode 360 and an auxiliary (or counter) electrode 370. The apparatus 300 also comprises a transparent surface 330, an analyte solution 340 and a light source 390.

In some embodiments, the reference electrode 360 and the auxiliary electrode 370 can be replaced by a reference/auxiliary electrode combination. The working electrode 380, the reference electrode 360, and the auxiliary electrode 370—or the working electrode 380 and the reference/auxiliary electrode combination—are in contact with the analyte solution 340 on the transparent surface 330. In one embodiment, the analyte solution 340 is a drop of solution, ranging from 1 µL to 100 µL. In one embodiment, the light source 390, such as a visible, UV or NIR probe with a bundle of fiber-optic cables, is fixed to a clamp below the transparent surface 330 for spectral measurement and focused directly on the surface of the working electrode 380 or the drop of solution 340. However, the light source 390 is not limited to being positioned below the transparent surface 330 or fixed to a clamp, as it may be positioned elsewhere as part of the apparatus 300.

Figure 2C:
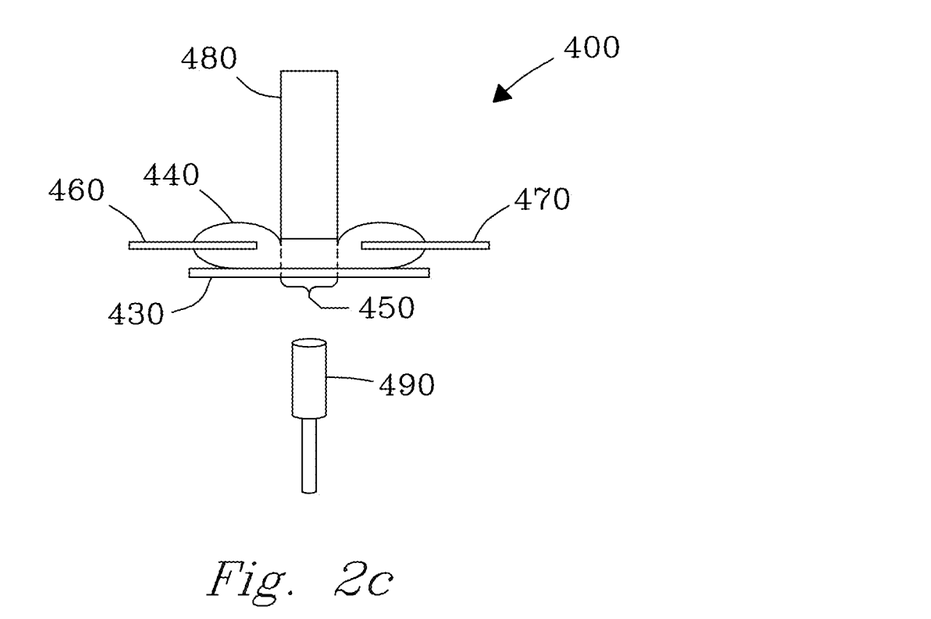
FIG. 2c is an illustration of an apparatus for simultaneous spectroelectrochemical analysis for thin layer set-up to measure redox potentials.

FIG. 2C is an illustration of an apparatus 400 for simultaneous spectroelectrochemical analysis for thin layer set-up to measure redox potentials. The apparatus 400 comprises a working electrode 480, a reference electrode 460 and an auxiliary (or counter) electrode 470. The apparatus 400 also comprises a transparent surface 430, an analyte solution 440 and a light source 490.

In some embodiments, the reference electrode 460 and the auxiliary electrode 470 can be replaced by a reference/auxiliary electrode combination. The working electrode 480, the reference electrode 460, and the auxiliary electrode 470—or the working electrode 480 and the reference/auxiliary electrode combination—are in contact with the analyte solution 440 on the transparent surface 430. A thin layer region 450 is observed as the working electrode is positioned closer to the transparent surface 430 thereby lowering the working volume. In one embodiment, the analyte solution 440 is a drop of solution, ranging from 1 µL to 100 µL. In one embodiment, the light source 490, such as a visible, UV or NIR probe with a bundle of fiber-optic cables, is fixed to a clamp below the transparent surface 430 for spectral measurement and focused directly on the surface of the working electrode 480 or the drop of solution 440. However, the light source 490 is not limited to being positioned below the transparent surface 430 or fixed to a clamp, as it may be positioned elsewhere as part of the apparatus 400.

Experimental Section

Chemicals and Materials

Potassium ferricyanide ($K_3[Fe(CN)_6]$), sodium ferrocyanide ($Na_4[Fe(CN)_6]$), tris-(2,2'-bipyridyl)ruthenium(II) dichloride hexahydrate [$(Ru(bpy)_3)Cl_2.6H_2O$] and potassium nitrate ($KNO_3$) were obtained from Sigma-Aldrich and used without further purification. Tris-(bis-(1,2-dimethylphosphinoethyl)rhenium(I) triflate ([Re(dmpe)$_3$](OTf)) was synthesized via a literature method.(34) Aqueous solutions of $K_3[Fe(CN)_6]$, $Na_4[Fe(CN)_6]$, and [Re(dmpe)$_3$](OTf) were made by dissolving the appropriate amount of reagent in 0.1 M $KNO_3$ solution. To make the glass slide's surface hydrophobic it was siliconized with Surfasil (Pierce Chemical Co.). Siliconization was done to ensure the formation of a spherical drop to allow a sufficiently large distance between the electrode surface and the glass slide to have semi-infinite diffusion on the time scale of a typical scan time for cyclic voltammetry.

Instrumentation

Cyclic voltammetry on the aqueous micro-drop was carried out using an Epsilon Potentiostat (Bioanalytical Systems) with a standard three-electrode cell stand from Bioanalytical Systems. All scans were recorded using a glassy carbon working electrode (area 7.07 mm$^2$) and a Pt wire auxiliary electrode. Between measurements, the working electrode was polished with 0.05 µm alumina slurry and a polishing pad, rinsed with distilled water, and wiped dry using a Kimwipe. All reported potentials are referenced versus a platinum wire quasi-reference electrode. Peak currents ($i_p$) were measured with respect to the extrapolated baseline current as described by Kissinger and Heineman.(35) UV-visible absorption spectra were recorded with a deuterium light source (Mikropack, model#DH 2000) and an Ocean Optics USB2000 detector (188-880 nm) using Spectra Suite Software for spectral data acquisitions. Emission spectra were recorded using a 532 nm laser excitation source (Melles Griot, 20 mW CW), coupled to an InSpectrum 150 spectrometer-CCD, and using SpectraSense data acquisition software. A 532 nm holographic notch filter (Kaiser) was used to reduce laser light backscattered into the InSpectrum 150 spectrometer. Signal integration times were typically 500 ms using a 2-mm slit width for a 600 gr/mm grating blazed at 500 nm. Step-index silica-on-silica optical fibers were purchased from Romack, Inc. The Ocean Optics system consisted of a USB-200FL spectrometer and Ocean Optics 00IBase32 Spectroscopy Software.

In a typical setup as illustrated in FIG. 2, a glass slide was placed on a stand above the reflectance probe. The custom designed stand consisted of two aluminum plates separated by an O-ring spacer to allow an optically transparent surface (e.g., quartz plate or glass microscope slide) to slide in. A hole was drilled at the center of the aluminum plates to permit passage of the optical beam. The upper aluminum plate was held in place with thumb screws that also provided conducting surfaces to attach the reference and working electrodes. The auxiliary and reference wire electrodes were spaced approximately 1 mm apart from one another. To ensure that the electrodes were relatively immobile during the entire course of the experiment, they were glued to the posts with epoxy resin. This limited the free mobility of the reference and the auxiliary electrodes, and preserved the relative distance, alignment, and orientation between the individual electrodes. The working electrode was lowered to within ~1 mm from the glass surface, and a 30 µL drop of solution was placed in between. The distance of the tip of the working electrode from the glass surface was set at 1 mm (which equals half the total optical path length) using slide calipers. The path length determined from the absorbance at 420 nm of a microdrop of a solution containing a known concentration of $K_3Fe(CN)_6$, confirmed the distance to within 5% of experimental error. The drop was positioned to cover the reference and auxiliary electrodes while surface tension ensured its contact with the working electrode from above. A 180° back-reflectance UV-visible-NIR probe with a bundle of fiber-optic cables was fixed to a clamp directly below the glass slide surface for spectral measurement and focused directly on the surface of the working electrode. The reflectance probe configuration was six peripheral fiber optic cables for excitation coming from the light source, with one concentrically located cable for collection of the light transmitted after reflection from the surface of the disk working electrode, going to the detector.

Results and Discussion

To explore this technique, three model compounds with known electrochemical and spectroscopic properties were chosen. The chemical systems used to demonstrate the microdrop technique were an absorbance based ionic probe [Fe(CN)$_6$]$^{3-/4-}$ and two luminescence based ionic probes [Re(dmpe)$_3$]$^{2+/+}$ and [Ru(bpy)$_3$]$^{3+/2+}$. All the three systems are characterized by a chemically reversible electrochemical couple and demonstrate the general requirements of absorbance and luminescence based systems, respectively. The viability of the technique to measure diffusion coefficients is demonstrated by using SILD spectroelectrochemistry on the [Fe(CN)$_6$]$^{3-/4-}$ and [Re(dmpe)$_3$]$^{2+/+}$ probes, while the ability of the technique to determine redox potentials by Nernstian analysis is demonstrated using absorbance based spectroelectrochemistry on [Fe(CN)$_6$]$^{3-/4-}$ system and emission based spectroelectrochemistry on [Ru(bpy)$_3$]$^{3+/2+}$ system.

[Fe(CN)$_6$]$^{3-}$/[Fe(CN)$_6$]$^{4-}$ System

For absorbance experiments, the [Fe(CN)$_6$]$^{3-}$/[Fe(CN)$_6$]$^{4-}$ couple ($E^{o\prime}$=0.25 V vs Ag/AgCl) was chosen. The two redox forms are spectroscopically distinguishable; an aqueous solution of [Fe(CN)$_6$]$^{4-}$ (pH=7, T=25° C.) is optically transparent at 420 nm while [Fe(CN)$_6$]$^{3-}$ has a strong absorption band at this wavelength under identical conditions ($E_{420}$=1040 M$^{-1}$ cm$^{-1}$).(36) Thus, oxidation of Fe(II) to Fe(III) results in the appearance of the 420 nm band, while the reduction of [Fe(CN)$_6$]$^{3-}$ back to [Fe(CN)$_6$]$^{4-}$ results in a decrease in its intensity. The redox couple was used to investigate both SILD and TL spectroelectrochemical behavior. For investigating SILD behavior, a total volume of 60 µL of solution was used, while for exploring TL behavior, a total volume of 30 µL of solution was used.

Cyclic Voltammetry of [Fe(CN)$_6$]$^{3-}$/[Fe(CN)$_6$]$^{4-}$

Figure 3A:
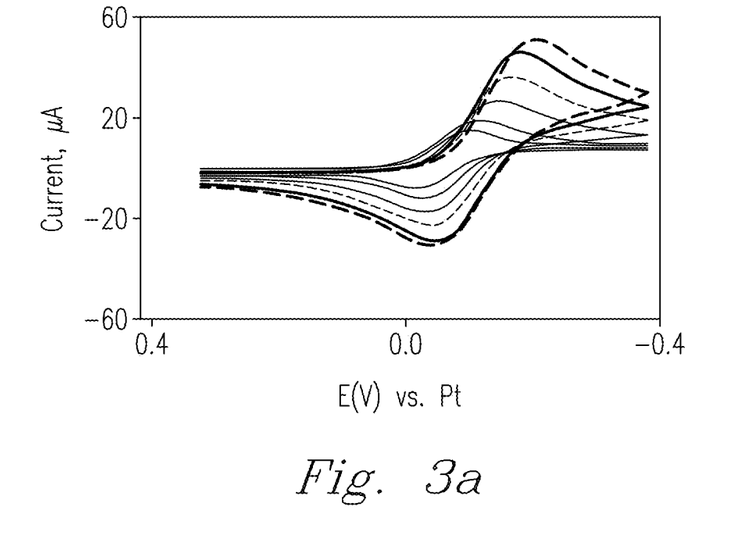
FIG. 3a shows cyclic voltammograms of an aqueous solution of $5.0\times10^{-3}$ M $K_3[Fe(CN)_6]$, 0.1 M $KNO_3$ as a function of scan rate, 5 (innermost voltammogram), 10, 25, 50, 75, and 100 mV/s (outermost voltammogram).

Cyclic voltammetry was used to evaluate the electrochemical properties of the cell, measure $E^{o\prime}$, and determine the diffusion coefficients of the [Fe(CN)$_6$]$^{3-}$/[Fe(CN)$_6$]$^{4-}$ system. The $E^{o\prime}$ for the system enclosed within a 60 µL drop was 0.1 V vs the quasi-reference electrode for all scans with a $\Delta E_P$=120 mV (v=50 mV s$^{-1}$). This $\Delta E_p$ is larger than the expected 59 mV for an electrochemically reversible 1e$^-$ system and is attributed to the slow electron transfer that can occur at glassy carbon. Cyclic voltammograms of 5.0 mM $K_3$[Fe(CN)$_6$] in 0.1 M KNO$_3$ solution as a function of scan rate (FIG. 3A) have voltammograms that are consistent with semi-infinite diffusion for scan rates ranging from 5 to 100 mV s$^{-1}$.(37) The positive shift in the potential of both the reduction and the oxidation peaks is due to the change in concentration of the oxidative and reductive species with respect to the Pt quasi-reference electrode. This was further confirmed by a control experiment where the cyclic voltammetry of a 5.0 mM $K_3$[Fe(CN)$_6$] in 0.1 M KNO$_3$ solution in a standard cell referenced to a Pt quasi reference electrode was compared to that using a Ag/AgCl reference electrode. The potential for both peaks again shifted in a positive direction when the Ag/AgCl reference electrode was replaced by the Pt quasi reference.

Figure 3B:
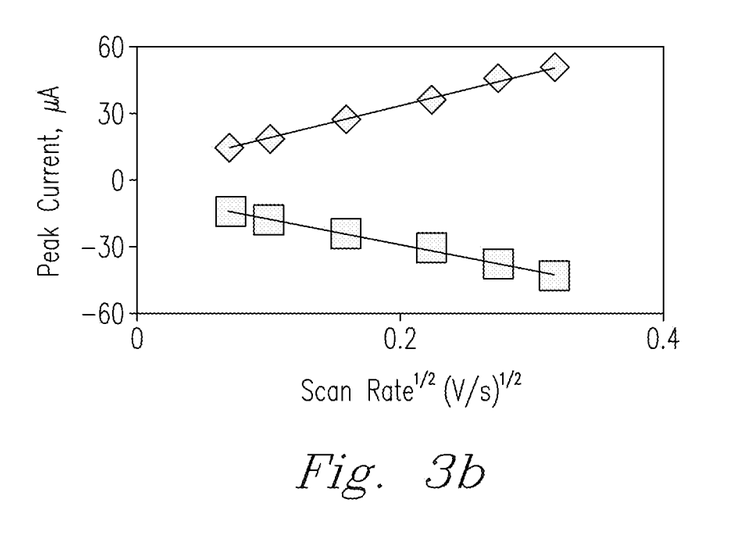
FIG. 3b is a plot of peak current versus the square root of scan rate: (squares) anodic wave; $i_{pa}(\mu A) = -114\ v^{1/2}\ (V\ s^{-1})^{1/2} - 6.1\ (R^2=0.997)$; (diamonds) cathodic wave; $i_{pc}(\mu A) = 149\ v^{1/2}(V\ S^{-1})^{1/2} + 3.9 (R^2=0.997)$.

A plot of peak currents versus the square root of scan rates (FIG. 3B) is linear as expected for semi-infinite diffusion. Using the RandleSevcik equation (35) the diffusion coefficient for [Fe(CN)$_6$]$^{3-}$ was found to be 2.4×10$^{-5}$ cm$^2$ which is in agreement with the literature.(38) The peak current ratio of $i_p/i_c$=0.76 indicates that the [Fe(CN)$_6$]$^{3-}$/[Fe(CN)$_6$]$^{4-}$ redox couple is quasi-reversible. The quasi-reversibility is indicative of adsorption of Analyte to the surface of the glassy carbon from the solution.(39) The performance is very similar to that obtained using a glassy carbon working electrode in a conventional regular volume three component electrochemical cell setup and confirms the semi-infinite linear diffusion, even at slower scan rates.

Figure 4A:
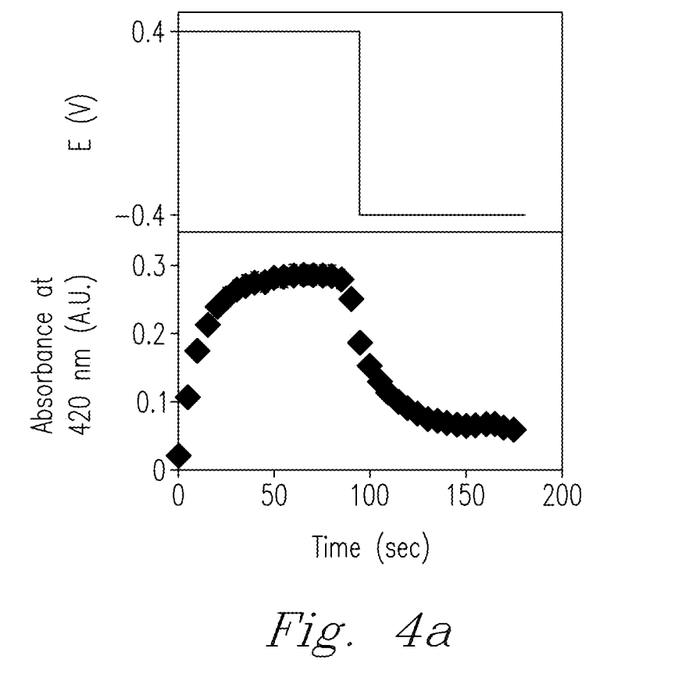
FIG. 4a shows double potential step chronoabsorptometry at 420 nm of an aqueous solution of $25.0\times10^{-3}$ M $Na_4[Fe(CN)_6]$, 0.1M $KNO_3$.

Chronoabsorptometry of [Fe(CN)$_6$]$^{3-}$/[Fe(CN)$_6$]$^{4-}$ Enclosed within a 60 µL Drop Double potential step chronoabsorptometry was used to evaluate if the technique can be used to explore SILD electrochemical behavior. In a typical experiment, a forward step of 0.4 V was applied to an aqueous solution of 25 mM [Fe(CN)$_6$]$^{4-}$, 0.1 M KNO$_3$ for 90 s while absorption spectra were concurrently recorded at 5 s intervals. The oxidation of [Fe(CN)$_6$]$^{4-}$ to [Fe(CN)$_6$]$^{3-}$ was characterized by the appearance and growth of the 420 nm absorption band. Subsequently, the reverse step to −0.4 V for 90 s resulted in a decrease in intensity of this absorption band, demonstrating a reduction of [Fe(CN)$_6$]$^{3-}$ back to [Fe(CN)$_6$]$^{4-}$. A plot of absorbance versus time at 420 nm for both forward and reverse potential steps is shown in FIG. 4A. It can be seen that the system levels off to a maximum absorbance within 40 s from the start of the oxidation while a minimum value is reached within 40 s of the start of the back reduction. Using the equation:

$$\delta = (2Dt)^{1/2} \quad (1)$$

where δ is the Nernst diffusion layer, D is the diffusion coefficient of ferrocyanide, and t is time, it is calculated that the electrolysis should take about 60 min. This calculated time for complete electrolysis confirms that under our experimental parameters, where each potential was held for less than 2 min, only a small fraction of the total volume of the working solution was electrolyzed, and semi-infinite diffusion conditions existed.

Thus, the leveling off of absorbance in the forward step of FIG. 4A is not due to complete electrolysis of the absorbing species, but rather is attributed to the optical configuration of the cell. The reflectance probe surface, composed of a fiber bundle 2 mm in diameter, illuminates the glassy carbon electrode (GCE), whose surface area is 3 mm in diameter, located a distance of 1 mm away from each other. At this distance, the reflectance probe beam divergence is larger than the active area of the GCE, and under the existing experimental settings, the spectroscopically interrogated solution volume includes solution outside of the diffusion layer adjacent to the GCE. Under these conditions, Beer's Law behavior will not strictly be observed, which explains why the change in absorbance in FIG. 4A levels off more rapidly than otherwise would be predicted. Using a larger electrode surface area or a more collimated beam would reduce this effect. Additionally, by continuing the measurement for longer than 5 min the gradual evaporation of the drop was observed, as evidenced by an increase in the absorbance intensity of the plateau even while holding the potential of the working electrode at −0.4 V.

Figure 4B:
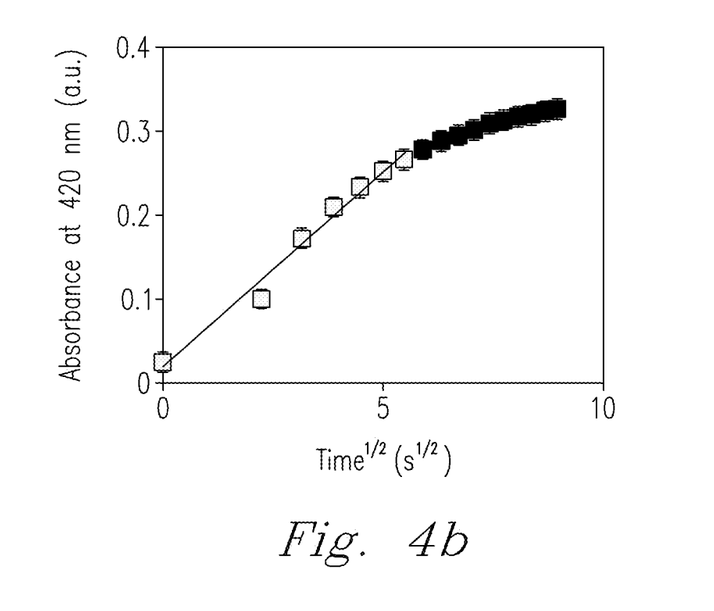
FIG. 4b is a plot of Absorbance vs $Time^{1/2}$, for the oxidation of $25.0\times10^{-3}$ M $Na_4[Fe(CN)_6]$, 0.1 M $KNO_3$. The equation for the diffusion controlled region is $A(a.u.) = 0.047\ t^{1/2}\ (s^{1/2}) + 0.02\ (R^2 = 0.98)$. The standard errors for the slope and intercept are (+0.002, −0.007) and (±0.006), respectively.

A plot of absorbance versus the square root of time for the oxidation process is shown in FIG. 4B. From this plot it can be seen that the absorbance change starts as a diffusion controlled system, but at approximately 40 s there is a deviation from the diffusion controlled system for the reasons discussed above. Applying the equation for chronoabsorptometry to the slope of the linear portion of the graph (FIG. 4B) that adheres to Beer's Law:

$$A = \frac{2\varepsilon_0 D^{\frac{1}{2}} C t^{\frac{1}{2}}}{\pi^{\frac{1}{2}}} \quad (2)$$

where A is the absorbance, $\varepsilon_o$ is the molar absorptivity of ferricyanide, D is defined from eq. 1, C is the concentration of ferrocyanide, and t is time; the molar absorptivity of ferricyanide was calculated be $\varepsilon_{420\,nm}$=1390 $M^{-1}$ $cm^{-1}$.(40, 41) This is similar to the accepted value of 1100 M $cm^{-1}$(42) and confirms the semi-infinite diffusion conditions.

Figure 7A:
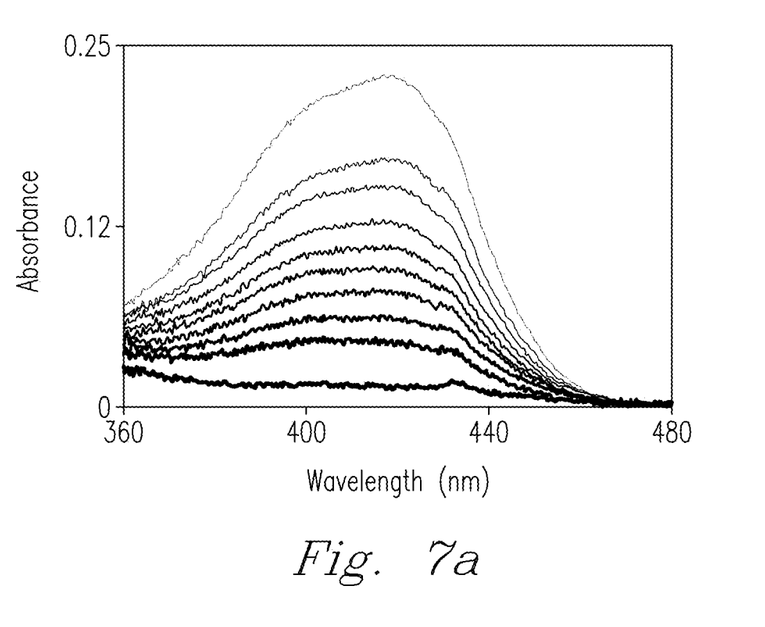
FIG. 7a shows absorbance spectra of $5.0\times10^{-3}$ M $K_3[Fe(CN)_6]$ in an aqueous solution of 0.1 M $KNO_3$ recorded as a function of decreasing potential. The applied potentials (vs. Ag/AgCl) are (from top to bottom): 300 mV, 156 mV, 146 mV, 136 mV, 126 mV, 116 mV, 106 mV, 96 mV, 86 mV and −100 mV.

Spectroelectrochemical Determination of Redox Potential for $[Fe(CN)_6]^{3-}/[Fe(CN)_6]^{4-}$ Enclosed within a 30 μL Drop In order to determine if the technique can be used to explore "thin-layer" electrochemical behavior, absorbance based spectroelectrochemistry was performed at differential applied potentials where a 30 μL drop was sandwiched between the working electrode and the quartz slide substrate maintained at a separation of 1 mm from each other. In a typical experiment, the working potential was set to a given value ($E_{app}$), and the solution was allowed to reach equilibrium, which was inferred when the UV-visible absorption spectrum no longer changed over a 3-4 min period. Shown in FIG. 7A are the absorbance spectra for each potential as $E_{app}$ was increased in a stepwise fashion from the most positive to the most negative value, allowing for measurements on the essentially fully reduced ($[Fe(CN)_6]^{4-}$) and fully oxidized ($[Fe(CN)_6]^{3-}$) forms, as well as mixtures. Reversing the step direction or varying the step size gave the same spectral results.

Spectroelectrochemical titration data thus obtained was analyzed according to the Nernstian expression for a multielectron transfer reaction:

$$E_{app} = E^{O\prime} - \frac{0.0591}{n}\log\frac{[Red]}{[Ox]}$$

where $E^{O\prime}$ is the formal electrode potential, n is the number of electrons transferred, [Red] and [Ox] are the respective concentrations of the fully reduced and fully oxidized species. The ratio [red]/[ox] at applied potential $E_{app}$ was estimated from $(A_{ox}-A)/(A-A_{red})$, where A is the absorbance at a given wavelength. $A_{ox}$ is the absorbance of the fully oxidized $[Fe(CN)_6]^{3-}$, which was estimated from the absorbance at the most positive value of $E_{app}$ ($E_{app}$=0.3V; or [Ox]/[Red]>1000); $A_{red}$ is the absorbance of the fully reduced sample, which was estimated from the absorbance at the most negative value of $E_{app}$ ($E_{app}$=−0.1 V; or [Ox]/[Red]<0.001).

Figure 7B:
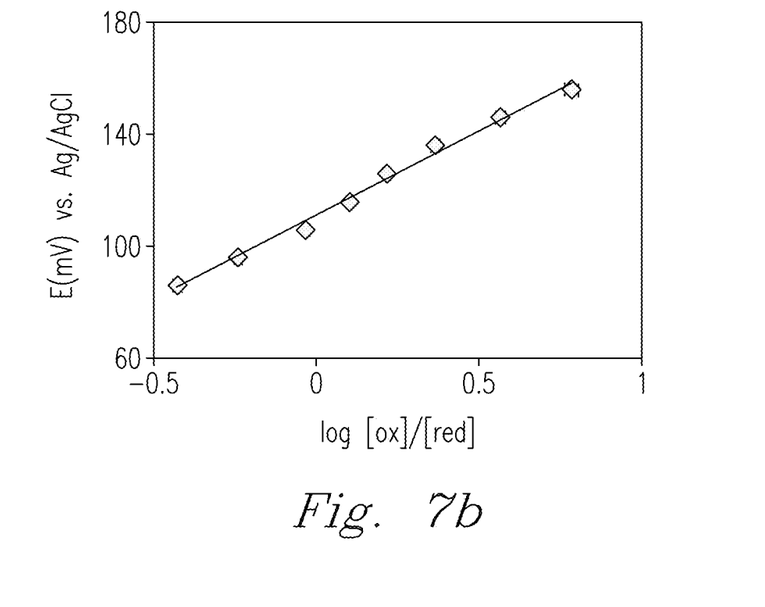
FIG. 7b is a Nernst plot of log [Ox]/[Red] vs. $E_{app}$ vs. Ag/AgCl at 420 nm. The equation of the line is $E_{app}(mV) = (60.2\pm4.7)$ log [Ox]/[Red] (mV) + $(131\pm4)$ (mV), $R^2=0.993$.

A plot of $E_{app}$ versus log [Ox]/[Red], shown in FIG. 7B, shows a linear correlation with an equation: $E_{app}$(mV)= 60.2±4.7 log [Ox]/[Red](mV)+131±4 (mV). The slope of 60.2 mV gives an n value of 0.983 (±0.10), confirming one electron transfer. The formal potential of the redox process as obtained from the y-intersept is consistent as that $E^{O\prime}$ obtained using cyclic voltammetry. This linearity is suggestive of ideal Nernstian behavior of the system which in turn is indicative of thin layer electrochemical and spectroelectrochemical behavior of the redox system in the present set-up.

$[Re(dmpe)_3]^{2+}/[Re(dmpe)_3]^+$ System

For emission based spectroelectrochemistry experiments in a SILD setup, $[Re(dmpe)_3]$(OTf) was chosen to take advantage of the changes in luminescence properties of the complex associated with the reversible $[Re(dmpe)_3]^{2+/+}$ ($E^{O\prime}$=0.34 V vs Ag/AgCl) redox couple. $[Re(dmpe)_3]^{2+}$ emits at 605 nm ($\lambda_{ex}$=532 nm) while $[Re(dmpe)_3]^+$ does not emit at this wavelength.(43) The complex has also been reported to exhibit a second redox process ($E^{O\prime}$=1.12 V vs Ag/AgCl; chemically quasi-reversible as determined by the ratio of the peak currents) assigned to the $Re^{3+/2+}$ couple. The total volume of solution used for the studies was 60 μL.

Cyclic Voltammetry of $[Re(dmpe)_3]^{2+}/[Re(dmpe)_3]^+$

Figure 5A:
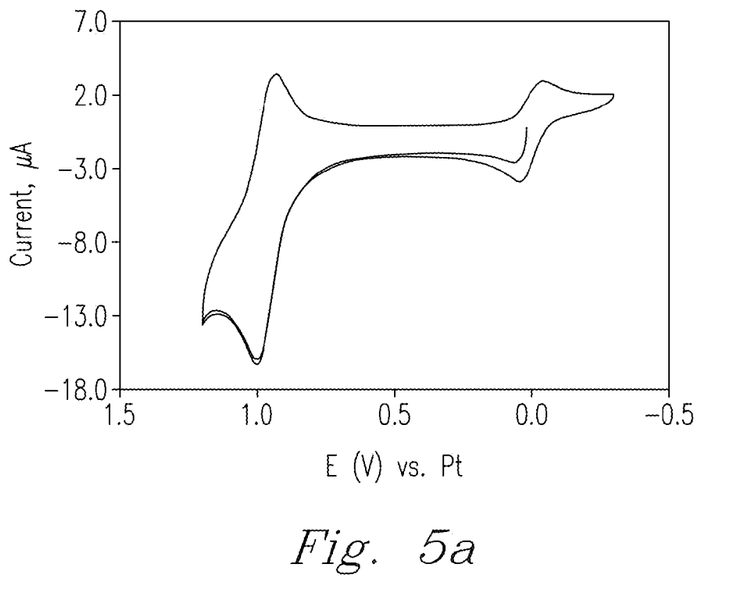
FIG. 5a shows a cyclic voltammogram of an aqueous solution of $1.25\times10^{-3}$ M $[Re(dmpe)_3](OTf)$, 0.1 M $KNO_3$ at v=50 mV $s^{-1}$ showing the two redox couples of $Re(dmpe)_3(OTf)$.
Figure 5B:
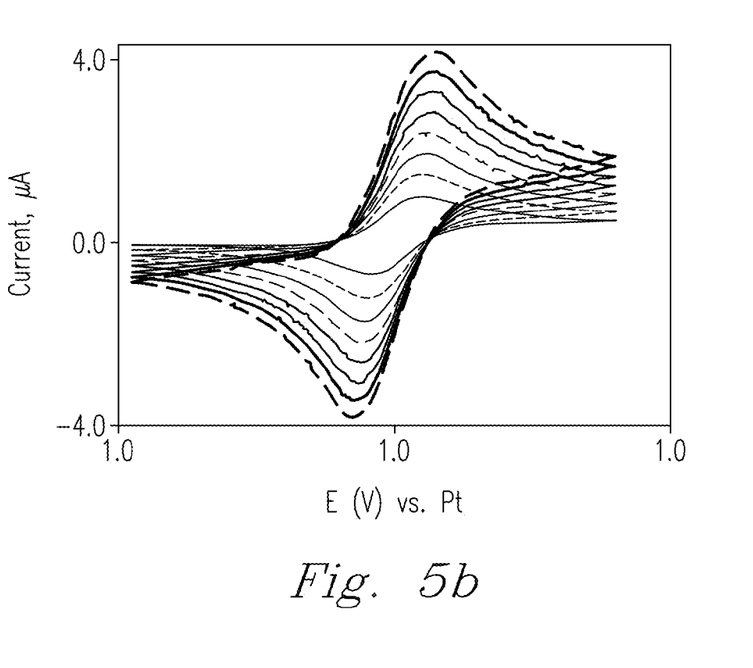
FIG. 5b shows cyclic voltammograms of an aqueous solution of $1.25\times10^{-3}$ M $Re(dmpe)_3(OTf)$, 0.1 M $KNO_3$ as a function of scan rate, 5(innermost voltammogram), 10, 15, 25, 36, 50, 65, and 80(outermost voltammogram) mV/s.
Figure 5C:
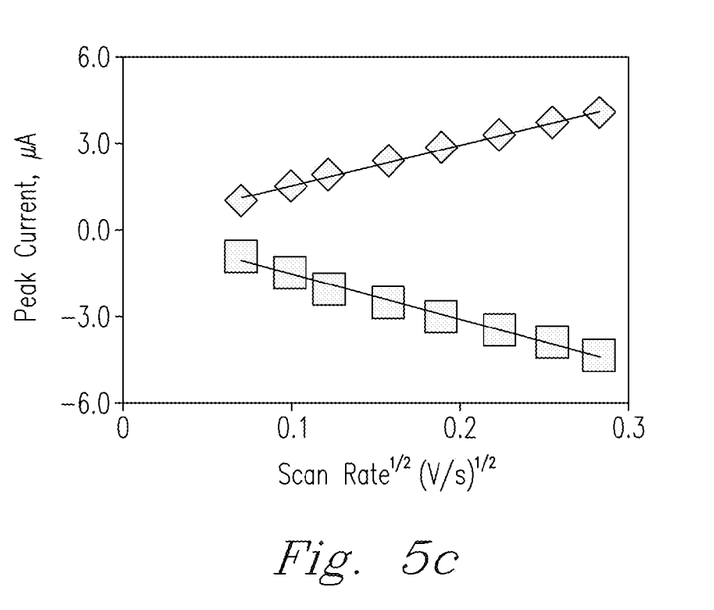
FIG. 5c is a plot of peak current versus the square root of scan rate: (solid squares) anodic process for $[Re(dmpe)_3]^{2+}/[Re(dmpe)_3]^+$; $i_{pa}(\mu A) = -15.6\ v^{1/2}(V\ S^{-1})^{1/2} - 0.8\ (R^2=0.997)$; (solid diamonds) cathodic process for $[Re(dmpe)_3]^{2+}/[Re(dmpe)_3]^+$; $i_{pc}(\mu A) = 14.1\ v^{1/2}(V\ s^{-1})^{1/2} + 0.005 (R^2=0.994)$.

Cyclic voltammetry was used to determine the $E^{O\prime}$ of both the $[Re(dmpe)_3]^{2+}/[Re(dmpe)_3]^+$ and $[Re(dmpe)_3]^{3+}/[Re(dmpe)_3]^{2+}$ couples as well as the diffusion coefficients for $[Re(dmpe)_3]^{2+}$ and $[Re(dmpe)_3]^+$. The cyclic voltammograms of the complex within the potential range 1.2 V and −0.3 V shows the two redox processes (FIG. 5A). The lower potential process ($E^{O\prime}$=0.002 V; $\Delta E_P$=87 mV) is assigned to the $[Re(dmpe)_3]^{2+}/[Re(dmpe)_3]^+$ couple while the higher potential process ($E^{O\prime}$=0.97 V; $\Delta E_p$=71 mV) is assigned to the $Re^{3+/2+}$ couple. Cyclic voltammograms as a function of scan rate for the $[Re(dmpe)_3]^{2+}/[Re(dmpe)_3]^+$ couple (FIG. 5B) have voltammograms that are consistent with semi-infinite diffusion for scan rates from 5 to 80 mV $s^{-1}$.(43) As expected, the increase in peak current is directly related to the increase in the square root of scan rate (FIG. 5C). The ratio of the slope of the peak currents as a function of square root of scan rate for the $[Re(dmpe)_3]^{2+}/[Re(dmpe)_3]$ couple is calculated to be $i_p/i_c$=0.90. It was expected that the $i_p/i_c$ would be less than one because of the air oxidation of $[Re(dmpe)_3]^+$ to $[Re(dmpe)_3]^{2+}$. Furthermore, a RandleSevcik analysis (35) showed that $[Re(dmpe)_3]^+$ has a diffusion coefficient of 4.34× $10^{-7}$ $cm^2$ $s^{-1}$. The diffusion coefficient of $[Re(dmpe)_3]^{2+}$ during its reduction to $[Re(dmpe)_3]^+$ is 3.53×$10^{-7}$ $cm^2$ $s^{-1}$. This performance is close to that obtained for a glassy carbon electrode dipped into a conventional electrochemical cell confirming semi-infinite diffusion, even at the slower scan rates. Because of significantly reduced chemical reversibility and significantly less pronounced changes in the spectroscopic properties, the $[Re(dmpe)_3]^{3+}/[Re(dmpe)_3]^{2+}$ couple was not further explored for the purpose of this paper.

Figure 6A:
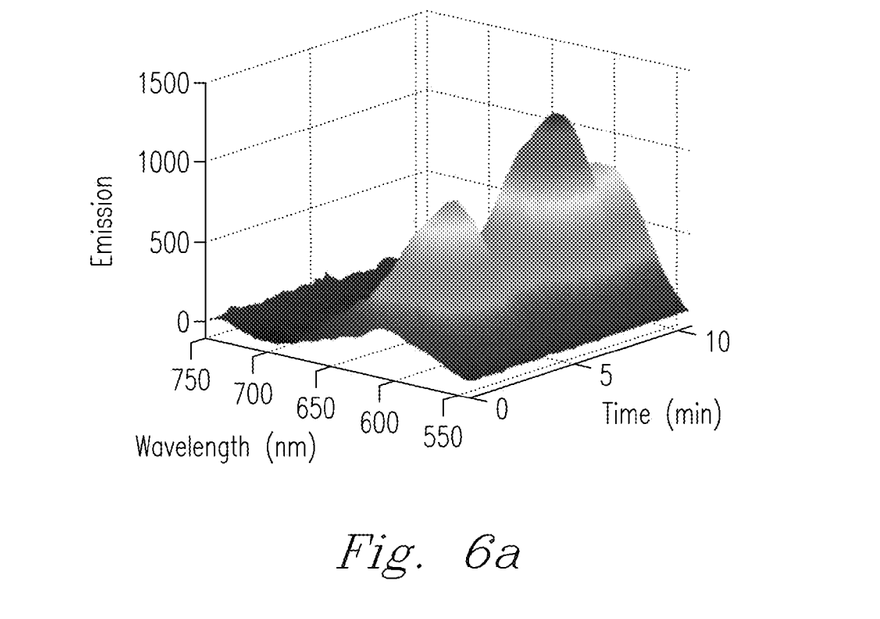
FIG. 6a shows modulation of luminescence intensity of an aqueous solution $1.25\times10^{-3}$ M $[Re(dmpe)_3](OTf)$, 0.1 M $KNO_3$ with time on the application of voltage ($\lambda_{ex}=532$ nm).

Luminescence Based Spectroelectrochemistry of $[Re(dmpe)_3]^{2+}/[Re(dmpe)_3]^+$ The cell's capacity for luminescence based spectroelectrochemistry was demonstrated using the $[Re(dmpe)_3]^{2+}/[Re(dmpe)_3]^+$ couple. Since $[Re(dmpe)_3]^+$ air oxidizes to $[Re(dmpe)_3]^{2+}$, a water-saturated $N_2$ blanket was placed over the working electrode assembly. A potential of 0.4 V was applied to an aqueous solution of 1.25 mM $[Re(dmpe)_3]$(OTf), 0.1 M KNO$_3$ for 90 s, and a series of luminescence spectra were recorded at 10 s intervals under 532 nm laser excitation. The oxidation of [Re(dmpe)$_3$]$^+$ to [Re(dmpe)$_3$]$^{2+}$ was characterized by the appearance and growth of the 605 nm emission band. An immediate change in potential to 0.6 V for 90 s resulted in a decrease in intensity of the 605 nm emission band, indicating reduction of [Re(dmpe)$_3$]$^{2+}$ back to the starting material, [Re(dmpe)$_3$]$^+$ (FIG. 6A).

Figure 6B:
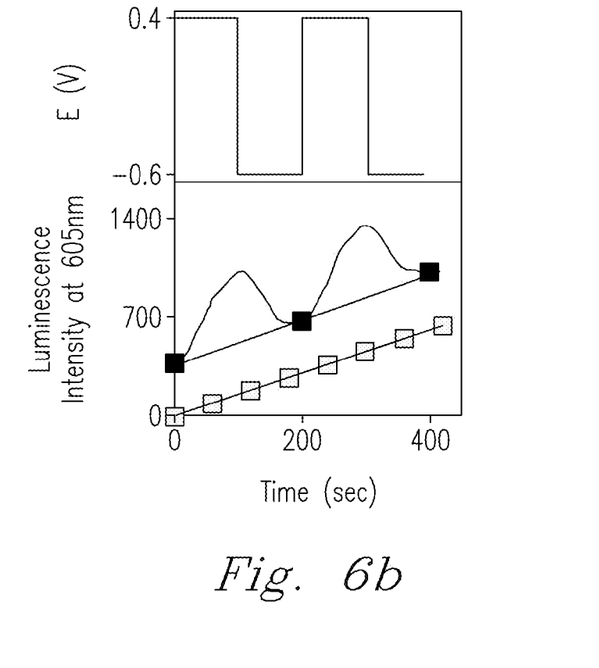
FIG. 6b shows modulation of luminescence intensity at 605 nm: (solid blue squares) Points at the trough of each modulation where there is a maximum concentration of $[Re(dmpe)]^+$ present. The equation of the line passing through the troughs of the modulation sinusoidal wave is $I(a.u.) = 1.60t(s) + 360$. Control run of solution $1.25\times10^{-3}$ M $[Re(dmpe)_3](OTf)$, 0.1 M $KNO_3$ where no voltage was applied is shown below. The equation of the line is $I(a.u.) = 1.50t(s)$.
Figure 6C:
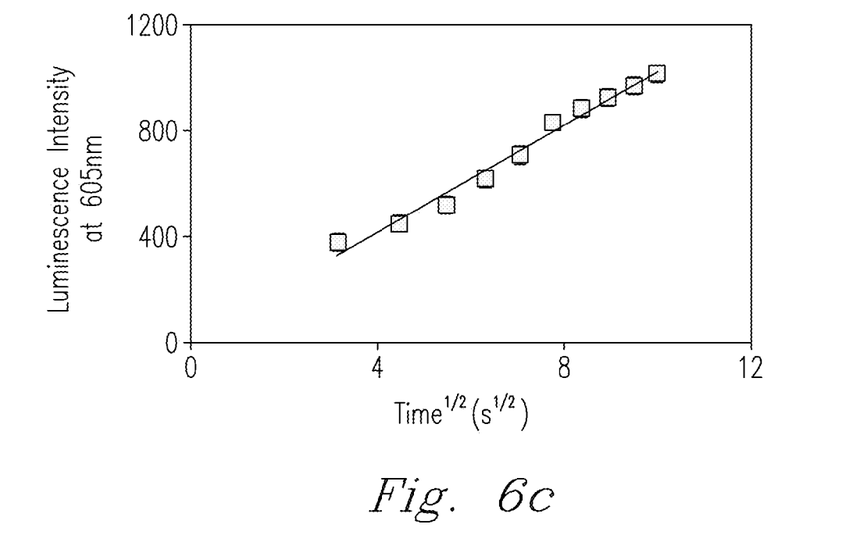
FIG. 6c is a plot of Luminescence vs $Time^{1/2}$ for the oxidation of $1.25\times10^{-3}$ M $[Re(dmpe)_3](OTf)$, 0.1 M $KNO_3$. The equation of the line is $I(a.u.) = 101t^{1/2}(s^{1/2}) + 9\ (R^2=0.98)$. The standard errors for the slope and intercept are (+1, −6) and (±10), respectively.

The profile of the emission maximum is shown in the time versus 605 nm emission intensity plot (FIG. 6B). Modulation of luminescence intensity at 605 nm by sequential application of a positive potential (0.4 V) for 120 s, followed by immediate application of a negative potential (−0.6 V) repeated for two cycles, showed a sinusoidal behavior in the intensity. The baseline slope (the line formed by extrapolation through the local intensity minima) showed a positive slope of 1.3. A control experiment conducted in which luminescence intensity of an aqueous solution of 1.25 mM [Re(dmpe)$_3$](OTf), 0.1 M KNO$_3$ was monitored under excitation by the same 532 nm laser source in the absence of any potential exhibited a similar slope (1.5), indicating the slope in the modulated curve is due to aerial oxidation. FIG. 6B shows the intensity vs time for the control run, illustrating that in the absence of an applied potential, there is a gradual appearance of the 605 nm emission band. We are currently working on modifications to reduce exposure to atmosphere to limit the chemical oxidation of air sensitive analytes. Shown in FIG. 6C is a plot of luminescence vs time$^{1/2}$ for the first oxidation of [Re(dmpe)$_3$]$^{2+}$. The linear plot confirms semi-infinite diffusion throughout the step.

[Ru(bpy)$_3$]$^{3+}$/[Ru(bpy)$_3$]$^{2+}$ System

To explore the ability of the technique for luminescence based TL spectroelectrochemical measurements, [Ru(bpy)$_3$]Cl$_2$·6H$_2$O was chosen to take advantage of the changes in emission properties of the complex associated with the reversible [Ru(bpy)$_3$]$^{3+/2+}$ (E$^{o'}$=1.05 V vs. Ag/AgCl) redox couple. [Ru(bpy)$_3$]$^{2+}$ emits at 620 nm (λex=532 nm) while [Ru(bpy)$_3$]$^{3+}$ does not emit at this wavelength under similar excitation. For these experiments, the total volume of solution chosen was 30 μL.

Cyclic Voltammetry of [Ru(bpy)$_3$]$^{3+}$/[Ru(bpy)$_3$]$^{2+}$

FIG. 4 shows the CV of 5 mM [Ru(bpy)$_3$]$^{2+}$ in an aqueous 0.1 M KNO$_3$ solution at a Pt working electrode (v=1 mVs$^{-1}$). The oxidation peak maximum is at 0.935 V and the reduction peak maximum is at 0.845 V resulting in E$^{o'}$=0.89 V (ΔE=90 mV).

Luminescence Based Spectroelectrochemistry of [Ru(bpy)$_3$]$^{3+}$/[Ru(bpy)$_3$]$^{2+}$ In order to evaluate the spectroelectrochemical characteristics of [Ru(bpy)$_3$]$^{3+}$/[Ru(bpy)$_3$]$^{2+}$ system, luminescence based spectroelectrochemistry was employed. A potential of 1.0 V was applied to an aqueous solution of 5 mM [Ru(bpy)$_3$]$^{2+}$ in 0.1 M KNO$_3$ and luminescence spectra were collected every 15 s till no further noticeable decrease in the emission intensity of the 620 nm band was observed. The complete disappearance of the band occurred in 3 min indicating that [Ru(bpy)$_3$]$^{2+}$ was completely electrolyzed to [Ru(bpy)$_3$]$^{3+}$.

Figure 8A:
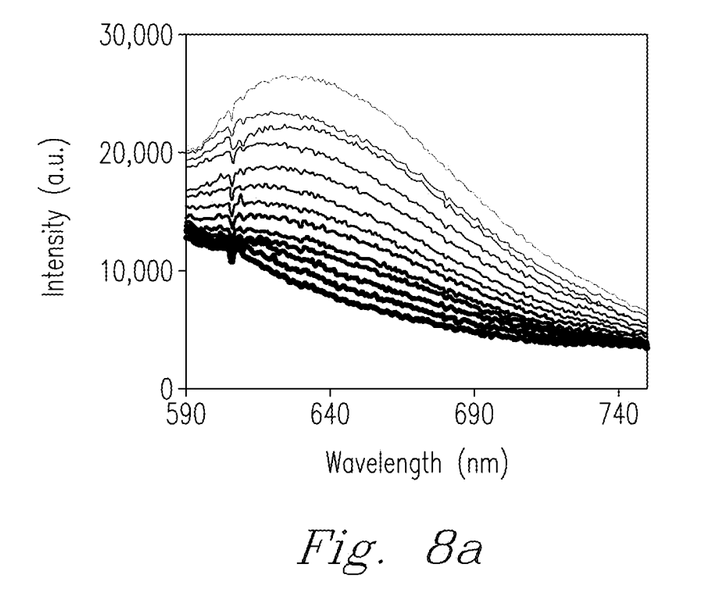
FIG. 8a shows emission spectra of $5.0\times10^{-3}$ M $[Ru(bpy)_3]^{2+}$ in an aqueous solution of 0.1 M $KNO_3$ recorded as a function of increasing potential. The applied potentials (vs. Ag/AgCl) are (from top to bottom): 700 my, 840 mV, 850 mV, 860 mV 870 mV, 880 mV, 890 mV, 900 mV, 910 mV, 920 mV, 930 mV, 940 mV and 1000 mV.

Spectroelectrochemical Determination of Redox Potential for [Ru(bpy)$_3$]$^{3+}$/[Ru(bpy)$_3$]$^{2+}$ Enclosed within a 30 μL Drop In a slight modification to the [Fe(CN)$_6$]$^{3-}$/[Fe(CN)$_6$]$^{4-}$ system mentioned in sections [0054-0057] above, luminescence based spectroelectrochemistry was performed at differential applied potentials where a 30 μL drop was sandwiched between the working electrode and the quartz slide substrate maintained at a separation of 1 mm from each other, to further validate that the systems investigated with the present set-up follow true "thin-layer" electrochemical behavior. In a typical experiment, the working potential was set to a given value (E$_{app}$), and the solution was allowed to reach equilibrium, which was inferred when the emission spectra no longer changed over a 3-4 min period. Shown in FIG. 8A are the luminescence spectra for each potential as E$_{app}$ was increased in a stepwise fashion from the most negative to the most positive value, allowing for measurements on the essentially fully reduced ([Ru(bpy)$_3$]$^{2+}$) and fully oxidized ([Ru(bpy)$_3$]$^{3+}$) forms, as well as mixtures. Reversing the step direction or varying the step size gave essentially the same spectral results. Spectroelectrochemical titration data thus obtained was analyzed according to the Nernstian expression for a multielectron transfer reaction (Equation (1)). In a slight modification to the system mentioned above, here the ratio [red]/[ox] at applied potential E$_{app}$ was estimated from (I$_{ox}$−I)/(I−I$_{red}$), where I is the luminescence at a given wavelength. I$_{ox}$ is the luminescence of the fully oxidized [Ru(bpy)$_3$]$^{3+}$, which was estimated from the luminescence at the most positive value of E$_{app}$ (E$_{app}$=1.0 V; or [ox]/[Red]>1000); I$_{red}$ is the luminescence of the fully reduced sample [Ru(bpy)$_3$]$^{2+}$, which was estimated from the luminescence at the most negative value of E$_{app}$ (E$_{app}$=0.70 V; or [Ox]/[Red]<0.001).

Figure 8B:
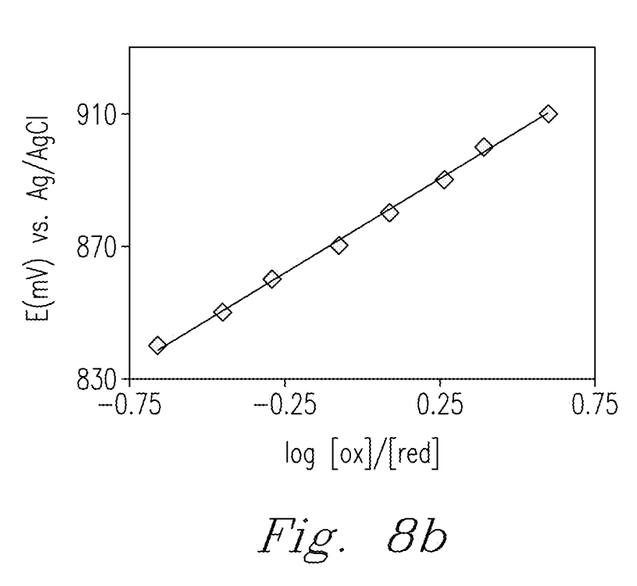
FIG. 8b is a Nernst plot of log [Ox]/[Red] vs. $E_{app}$ vs. Ag/AgCl at 620 nm. The equation of the line is $E_{app}(mV) = (56.5\pm4.4)$ log [Ox]/[Red] (mV) + $(876\pm4)$ (mV), $R^2=0.996$.

A plot of E$_{app}$ versus Log [Ox]/[Red], shown in FIG. 8B, shows a linear correlation with an equation: E$_{app}$ (mV)=56.5±4 Log [Ox]/[Red] (mV)+876±4 (mV). The slope of 56.5 mV gives an n value of 1.05 (±0.1), confirming an one electron transfer process. The formal potential of the redox process obtained from the y-intercept is consistent as that E$^{o'}$ obtained using cyclic voltammetry. This linearity is suggestive of ideal Nernstian behavior of the system which in turn is indicative of thin layer electrochemical and spectroelectrochemical behavior of the redox system in the present set-up.

Experimental Conclusions

SILD spectroelectrochemistry using either absorption or emission spectroscopy can be done on any microliter size, such as a 30 μL drop of liquid, with a cell that is easy to fabricate and use. SILD conditions were maintained over the time scale corresponding to cyclic voltammetry scan rates as slow as 2 mV s$^{-1}$. Optical sensitivity was sufficient to easily monitor absorbance and fluorescence changes associated with the electrochemistry. The cell has the advantage of not requiring electrode transparency, making it more widely applicable than spectroelectrochemical techniques in which optical measurements are made through the electrode. The cell could be easily converted into a TL cell by simply reducing the distance between the electrode and the bottom plate. Improvements that could be made include enlarging the electrode surface or reducing the optical beam so that only the diffusion layer is monitored and provision for deoxygenation. The effectiveness and reproducibility of this method for studying spectroelectrochemical processes in microquantities of analyte makes the technique promising for substances that are expensive, limited in available quantity, or pose disposal issues because of toxicity or radioactivity. It is possible to use the SILD setup to obtain diffusion coefficient values, and thin-layer setup can be used to obtain electrochemical potential E$^{o'}$, while changing only one parameter, the working volume of the solution.

REFERENCES

1. Kuwana, T.; Darlington, R. K.; Leedy, D. W. *Anal. Chem.* 1964, 3.6, 2023
2. Rieder, K.; Hauser, U.; Siegenthaler, H.; Schmidt, E.; Ludi, A. *Inorg. Chem.* 1975, 14, 1902

3. Rohrbach, D. F.; Heineman, W. R.; Deutsch, E. *Inorg. Chem.* 1979, 18, 2536
4. Hill, M. G.; Penneau, J. F.; Zinger, B.; Mann, K. R.; Miller, L. L. *Chem. Mater.* 1992, 4, 1106
5. Kaim, W.; Klein, A.; Hasenzahl, S.; Stoll, H.; Zalis, S.; Fiedler, J. *Organometallics* 1998, 17, 237
6. Toma, H. E.; Araki, K. *Curr. Org. Chem.* 2002, 6, 21
7. Lahiri, G. K.; Kaim, W. *Dalton Trans.* 2010, 39, 4471
8. Owens, J. L.; Marsh, H. A.; Dryhurst, G. *J. Electroanal. Chem.* 1978, 91, 231
9. Stutts, K. J.; Powell, L. A.; Wightman, R. M. *J. Electrochem. Soc.* 1981, 128, 1248
10. Heineman, W. R.; Norris, B. J.; Goelz, J. F. *Anal. Chem.* 1975, 47, 79
11. Sailasuta, N.; Anson, F. C.; Gray, H. B. *J. Am. Chem. Soc.* 1979, 101, 455
12. Larsson, T.; Lindgren, A.; Ruzgas, T. *Bioelectrochemisuy* 2001, 53, 243
13. Comtat, M.; Durliat, H. *Biosens. Bioelectron.* 1994, 9, 663
14. Heineman, W. R. *Anal. Chem.* 1978, 50, 390A
15. Strojek, J. W.; Kuwana, T. *J. Electroanal. Chem.* 1968, 16, 471
16. Kuwana, T.; Strojek, J. W. *Faraday Discuss.* 1968, 45, 134
17. Osa, T.; Kuwana, T. *J. Electroanal. Chem.* 1969, 22, 389
18. Bewick, A.; Tuxford, A. M. *Symp. Faraday. Soc.* 1970, 4, 114
19. Aylmer-Kelly, A. W. B.; Bewick, A.; Cantrill, P. R.; Tuxford, A. M. *Faraday Discuss.* 1973, 56, 96
20. Pruiksma, R. *J. Electroanal. Chem.* 1980, 114, 147
21. Gaillard, F.; Levillain, E. *J. Electroanal. Chem.* 1995, 398, 77
22. Hansen, W. N.; Kuwana, T.; Osteryoung, R. A. *Anal. Chem.* 1966, 38, 1810
23. Prostak, A.; Mark, H. B.; Hansen, W. N. *J. Phys. Chem.* 1968, 72, 2576
24. Kuwana, T.; Heineman, W. R. *Acc. Chem. Res.* 1976, 9, 241
25. Kuwana, T.; Winograd, N. Spectroelectrochemistry at Optically Transparent Electrodes. I. Electrodes under Semi-Infinite Diffusions ConditionsIn *Electroanalytical Chemistry*; Bard, A. J., Ed.; Marcel Dekker. New York, 1974; p 1.
26. Heineman, W. R.; Hawkridge, F. M.; Blount, H. N. Spectroelectrochemistry at Optically Transparent Electrodes. II. Electrodes under Thin-Layer and Semi-Infinite Diffusions Conditions and Indirect Coulometric TitrationsIn *Electroanalytical Chemistry*; Bard, A. J., Ed.; Marcel Dekker: New York, 1984; p 1.
27. Niu, J.; Dong, S. *Rev. Anal. Chem.* 1996, 15, 1
28. Winograd, N.; Kuwana, T. *J. Electroanal. Chem.* 1969, 23, 333
29. Winograd, N.; Kuwana, T. *Anal. Chem.* 1971, 43, 252
30. Porter, M. D.; Dong, S. J.; Gui, Y. P.; Kuwana, T. *Anal. Chem.* 1984, 56, 2263
31. Salbeck, J. *J. Electroanal. Chem.* 1992, 340, 169
32. Heineman, W. R.; Kuwana, T. *Anal. Chem.* 1972, 44, 1972
33. Wijayawardhana, C. A.; Halsall, H. B.; Heineman, W. R. *Anal. Chico. Acta* 1999, 399, 3
34. Deutsch, E.; Libson, K.; Vanderheyden, J. L.; Ketring, A. R.; Maxon, H. R. *Int. J. Radial. Appl. Insirum. B* 1986, 13, 465
35. Kissinger, P. T.; Heineman, W. R. *J. Chem. Educ.* 1983, 60, 702
36. Krenitsky, T. A.; Neil, S. M.; Elion, G. B.; Hitchings, G. H. *Arch. Biochem. Biophys.* 1972, 150, 585
37. Bard, A. J.; Faulkner, L. R. *Electrochemical Methods: Fundamentals and Applications*, 2nd ed; Wiley: New York, 2001; p 147.
38. Konopka, S. J.; McDuffie, B. *Anal. Chem.* 1970, 42, 1741
39. Yang, R.; Qian, Z.; Deng, J. *J. Electrochem. Soc.* 1998, 145, 2231
40. Ogura, K.; Naito, T. *Electrochim. Acta* 1982, 27, 1243
41. Bard, A. J.; Faulkner, L. R. *Electrochemical Methods: Fundamentals and Application*, 2 ed.; Wiley: New York, 2001; p 682.
42. Alexander, J. J.; Gray, H. B. *J. Am. Chem. Soc.* 1968, 90, 4260
43. Kirchhoff, J. R.; Allen, M. R.; Cheesman, B. V.; Okamoto, K.; Heineman, W. R.; Deutsch, E. *Inorg. Chim. Acta* 1997, 262, 195
44. T. P. DeAngelis, W. R. Heineman, *J. Chem. Edu.* 1976, 53, 594 597
45. S. Chatterjee, Cooperative Two-Electron Reagents of Lower Transition Metals of Group 10. Ph. D. Dissertation, University of Cincinnati, Cincinnati, Ohio, 2009.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. An apparatus for simultaneous spectroelectrochemical analysis comprising:
    a. a transparent surface;
    b. a reflective working electrode, a reference electrode, and an auxiliary electrode, wherein the electrodes are in contact with an analyte solution on the transparent surface, wherein the analyte solution has a total volume size of approximately 200 µl or less;
    c. a light source for focusing light on one of the following: a surface of the reflective working electrode and the analyte solution; and
    d. a detector for receiving the light,
    wherein the apparatus is open and adjustable.

2. The apparatus of claim 1 further comprising a cusp of customized volume to contain the analyte solution on the transparent surface.

3. The apparatus of claim 1 wherein the light of the light source is one of:
    visible light, ultraviolet (UV), near infrared (NIR) and combinations thereof.

4. The apparatus of claim 1 wherein the light is transmitted via a fiber optic cable.

5. The apparatus of claim 1 wherein the transparent surface is a transparent slide.

6. The apparatus of claim 5 wherein the transparent slide is made of glass or quartz.

7. The apparatus of claim 1 further comprising a first channel for placement of the reference electrode and a second channel for placement of the auxiliary electrode.

8. The apparatus of claim 1 further comprising a fastener for fixing in place the working electrode perpendicular to the transparent surface.

9. The apparatus of claim 1 further comprising a fastener for securing and providing electrical contact to the reference and auxiliary electrodes.

10. The apparatus of claim 1 wherein the reference and auxiliary electrodes are spaced from approximately 0.1 mm to approximately 3.0 millimeters apart from one another.

11. The apparatus of claim 1 wherein the working electrode is positioned less than 1 millimeter from the transparent surface.

12. A reflective spectroscopy method of simultaneous spectroelectrochemical analysis in an open and adjustable spectroelectrochemical cell, the method comprising:
   a. providing a transparent surface;
   b. contacting an analyte solution having a total volume size of approximately 200 µl or less on the transparent surface with a reflective working electrode, a reference electrode, and an auxiliary electrode;
   c. focusing light from a light source on one of the following: a surface of the reflective working electrode and the analyte solution; and
   d. detecting the light.

13. The method of claim 12 further comprising adjusting a potential of the working electrode and monitoring spectroscopic changes of the analyte solution that occur with changes in thermodynamic potentials.

14. The method of claim 12 further comprising containing the analyte solution in a cusp on the transparent surface.

15. The method of claim 12 wherein the light of the light source is one of:
   visible light, ultraviolet (UV), near infrared (NIR) and combinations thereof.

16. The method of claim 12 wherein the light is transmitted via a fiber optic cable.

17. The method of claim 12 wherein the transparent surface is a transparent slide.

18. The method of claim 17 wherein the transparent slide is made of glass or quartz.

19. The method of claim 12 further comprising placing the reference electrode in a first channel and the auxiliary electrode in a second channel.

20. The method of claim 12 further comprising fixing in place the working electrode perpendicular to the transparent surface.

21. The method of claim 12 further comprising securing and providing electrical contact to the reference and auxiliary electrodes.

22. The method of claim 12 further comprising spacing apart the reference and auxiliary electrodes from approximately 0.1 mm to approximately 3.0 millimeters from one another.

23. The method of claim 12 further comprising positioning the working electrode less than 1 millimeter from the transparent surface.

24. A reflective spectroscopy method of simultaneous spectroelectrochemical analysis in an open and adjustable spectroelectrochemical cell, the method comprising:
   a. providing a transparent surface;
   b. contacting an analyte solution having a total volume size of approximately 200 µl or less on the transparent surface with a reflective first electrode and a second electrode;
   c. focusing light from a light source on one of the following: a surface of the reflective first electrode and the analyte solution; and
   d. detecting the light reflected from one of the following: the surface of the reflective first electrode and the analyte solution.

25. The method of claim 24 wherein the first electrode is a working electrode and the second electrode is a reference/auxiliary electrode combination.

26. The method of claim 25 further comprising adjusting a potential of the working electrode and monitoring spectroscopic changes of the analyte solution that occur with changes in thermodynamic potentials.

27. The method of claim 24 further comprising contacting the analyte solution with a third electrode.

28. An apparatus for simultaneous spectroelectrochemical analysis comprising:
   a. a transparent surface;
   b. a reflective first electrode and a second electrode, wherein the electrodes are in contact with an analyte solution on the transparent surface, wherein the analyte solution has a total volume size of approximately 200 µl or less ;
   c. a light source for focusing light on one of the following: a surface of the reflective first electrode and the analyte solution; and
   d. a detector for receiving the light reflected from one of the following: the surface of the reflective first electrode and the analyte solution, wherein the light source and the detector are combined in a single unit,
   wherein the apparatus is open and adjustable.

29. The apparatus of claim 28 wherein the first electrode is a working electrode and the second electrode is a reference/auxiliary electrode combination.

30. The apparatus of claim 28 further comprising a third electrode, wherein the third electrode is in contact with the analyte solution.

* * * * *